United States Patent [19]

Panzer et al.

[11] 4,412,944
[45] Nov. 1, 1983

[54] HIGH FOAMING, LOW EYE IRRITATION CLEANING COMPOSITIONS CONTAINING ETHOXYLATED ANIONIC (C13-C30) SULPHATES

[75] Inventors: George W. Panzer, Timonium; Louis J. Nehmsmann, Ellicott City, both of Md.

[73] Assignee: Alcolac, Inc., Baltimore, Md.

[21] Appl. No.: 280,369

[22] Filed: Jul. 6, 1981

Related U.S. Application Data

[63] Continuation of Ser. No. 120,762, Feb. 12, 1980, abandoned.

[51] Int. Cl.$^3$ ............................................. C11D 1/29
[52] U.S. Cl. ............................ 252/551; 252/DIG. 5; 252/DIG. 13; 424/70
[58] Field of Search ............... 252/117, 121, 153, 526, 252/532, 541, 545, 551, DIG. 5, DIG. 13, DIG. 14

[56] References Cited

U.S. PATENT DOCUMENTS

| | | | |
|---|---|---|---|
| 3,150,098 | 9/1964 | Wilson | 252/551 |
| 3,468,805 | 9/1969 | Grifo | 252/551 |
| 3,562,170 | 2/1971 | Zorayan | 252/152 |
| 3,658,727 | 4/1972 | Mast | 252/538 |
| 3,812,041 | 5/1974 | Inamorato | 252/89 |
| 3,998,750 | 12/1976 | Payne | 252/108 |
| 4,072,632 | 2/1978 | Reed | 252/541 |
| 4,195,077 | 3/1980 | Marsh | 252/551 |
| 4,212,749 | 7/1980 | Kolbe | 252/551 |

FOREIGN PATENT DOCUMENTS

| | | | |
|---|---|---|---|
| 2350008 | 4/1974 | Fed. Rep. of Germany | 252/551 |
| 797119 | 6/1958 | United Kingdom | 252/551 |

*Primary Examiner*—Dennis L. Albrecht
*Attorney, Agent, or Firm*—Finnegan, Henderson, Farabow, Garrett & Dunner

[57] ABSTRACT

A high foaming, low eye irritation cleaning composition. The composition contains an alkyl ether sulfate having the following structural formulae:

$$R(A)_nOSO_3M \text{ or } R_1(A)_nSO_3M$$

wherein R is an alkyl, alkylaryl, acyl or alkenyl group having at least 13, preferably 13 to 30, most preferably 14 to 24, carbon atoms in the alkyl chain; $R_1$ is an acylamide group having at least 13, preferably 13 to 30, most preferably 14 to 24, carbon atoms, A is an alkyl ether group derived from ethylene oxide, propylene oxide, butylene oxide, glycidol and substituted epoxides, the preferred group being ethoxy; n is about 6 to about 100, preferably about 6 to about 20, more preferably about 10 to about 20; and M is a cation such as an alkali metal, an alkaline earth metal, a transition metal, ammonium, an alkylamine, or an alkanolamine. These compositions are particularly useful as cosmetic cleaning compositions, such as shampoos and bubble baths.

2 Claims, No Drawings

HIGH FOAMING, LOW EYE IRRITATION CLEANING COMPOSITIONS CONTAINING ETHOXYLATED ANIONIC (C13-C30) SULPHATES

This is a continuation application of patent application Ser. No. 120,762, filed Feb. 12, 1980 now abandoned.

BACKGROUND OF THE INVENTION

1. Field of the Invention

This invention relates to cleaning compositions, specifically cosmetic compositions such as shampoos, bubble baths and other bath products. More specifically, it relates to compositions having good foaming properties and very low eye irritation. The invention finds particular utility in the preparation of shampoos having a low level of eye irritation.

2. Description of the Prior Art

Cosmetic cleaning compositions, particularly those used as shampoos, should produce stable foams of high volume. The amount and stability of the foam are directly related to the perceived cleaning efficiency of the composition. In addition, these compositions should produce little or no irritation to the eyes and skin.

Anionic surfactants, such as anionic sulfates, have excellent cleaning and foaming properties. As a result, many shampoos and other cosmetic cleaning compositions contain anionic sulfates. However, the anionic sulfates at concentrations used in these compositions irritate the skin and eyes. Therefore, they must be modified or combined with other reagents in order to reduce the irritation to a level which is commercially acceptable.

It is known that the irritation caused by anionic sulfates can be reduced by ethoxylation. However, this reduction in irritation is accompanied by a corresponding reduction in foam volume. Thus, sodium lauryl sulfate, a high foaming surfactant, causes significant eye irritation. In contrast, sodium laureth-12 sulfate (sodium lauryl ether (12) sulfate) is almost completely non-irritating, but is a poor foaming agent. (See Schoenberg, "Baby Shampoo," Household & Personal Products Industry 60 (September 1979).) The poor foaming properties of ethoxylated alkyl sulfates is reported in many other publications. For example, U.S. Pat. No. 4,132,678 discloses that the foaming properties of alkyl ($C_{10}$-$C_{18}$) sulfates is drastically reduced if more than five ethoxy groups are added to the molecule.

Prior to this invention, shampoos having both low irritation and good foaming properties were made by combining a good foaming agent with an anti-irritant. One example of this type composition is found in Schoenberg where a blend of sodium laureth-12 sulfate and cocamidopropyl betaine is reported to have eye irritation and foaming properties "on a par" with an unidentified national brand of baby shampoo.

A composition containing a surfactant betaine and an alkyl ether sulfate is also disclosed in U.S. Pat. No. 3,950,417. This composition contains a long chain betaine-anionic surfactant complex in combination with a highly soluble non-anionic polyoxyethylene sorbitan ester. The preferred betaine-anionic surfactant complex is a combination of cocamidobetaine and tridecyl (4.4) ether sulfate. The preferred polyoxyethylene sorbitan ester is polyoxyethylene (44) sorbitan monolaurate. Although the patent is silent on the purpose of the polyoxyethylene sorbitan ester, its purpose presumably is to reduce the irritation caused by the betaine-anionic complex. (See Norda Briefs No. 479 (March 1977).) Polyoxyethylene (20) sorbitan monolaurate is the anti-irritant that is used in a commercial baby shampoo. (Id.)

Another composition containing alkyl ether sulfates which is allegedly nonirritating is disclosed in U.S. Pat. No. 4,110,263. Here an alkyleneoxylated bisquarternary ammonium compound is said to decrease the occular irritancy produced by anionic detergents and permit formulation of compositions to maximize cleaning properties. Among the anionic detergents disclosed are tridecyl ether (4) sulfate and tetradecyl ether (3) sulfate.

SUMMARY OF THE INVENTION

It has now been discovered that alkyl ether sulfates having at least 13 carbon atoms and at least six alkyloxy groups unexpectedly produce high volume and stable foams and, at the same time, have low irritation properties. Therefore, high foaming-low eye irritation cleaning compositions can be produced with these alkyl ether sulfates without the need for additional foaming or irritation reducing agents. These agents can, however, be added to provide greater foaming or to reduce irritation levels.

DESCRIPTION OF THE PREFERRED EMBODIMENTS

The anionic ether sulfates of the present invention have the following structural formulae:

$$R(A)_nOSO_3M \qquad (I)$$

or $$R_1(A)_nSO_3M \qquad (II)$$

wherein R is an alkyl, alkylaryl, acyl, or alkenyl group having a least 13, preferably 13 to 30, most preferably 14 to 24, carbon atoms in the alkyl, acyl or alkenyl chain; $R_1$ is an acylamido group having at least 13, preferably 13 to 30, most preferably 14 to 24, carbon atoms; A is an alkyl ether group derived from ethylene oxide, propylene oxide, butylene oxide, glycidol and substituted epoxides, the preferred group being ethoxy; n is about 6 to about 100, preferably about 6 to about 20, more preferably about 10 to about 20; and M is a cation such as an alkali metal, an alkaline earth metal, a transition metal (preferably Fe, Mn, Cu, Zr or Zn), ammonium, an alkylamonium, or an alkanolamonium. The preferred cations are sodium, potassium, magnesium, calcium, ammonium and mono-, di- and tri-ethanol ammonium.

The benefits of this invention can be obtained from the use of a single anionic ether sulfate having a chain length and alkyloxylation within the parameters of Formulae I or II. They can also be obtained by the use of mixtures of anionic ether sulfates having the requisite chain length and alkyloxylation. Moreover, while best results are obtained when all of the anionic ether sulfates have alkyl, acyl, or alkenyl groups containing at least 13 carbon atoms, satisfactory results will be obtained if at least 45%, but preferably at least 50%, of the compounds have the characteristics required by Formulae I or II.

The preferred compounds which are useful in this invention are myristyl ether sulfates, oleyl ether sulfates, stearyl ether sulfates, cetyl ether sulfates and mixtures of these compounds.

A mixture containing about 60% sodium myristyl ether (12) sulfate and about 40% sodium cetyl ether (12) sulfate provided excellent results. Similar results were also obtained with a mixture containing about 65% sodium cetyl ether (12) sulfate and about 35% sodium stearyl ether (12) sulfate.

Many of the anionic ether sulfates of this invention and mixtures of these compounds can be purchased from commercial sources. Alternatively, they can be synthesized by techniques known in the art. For example, the alkyl ether sulfates can be prepared by sulfating aliphatic straight or branched chain alcohols or alkyl phenols having the appropriate number of carbon atoms in the alkyl group and sufficient ethoxylation. These alcohols and mixtures thereof are commercially available.

The anionic ether sulfate should be present in the cosmetic cleaning composition in an amount of from about 15% to about 50% of the total weight of the composition. Concentrated and semisolid compositions such as gels and creams generally have higher amounts.

The cosmetic cleaning composition will also include minor amounts of other conventional ingredients. These include colorants, preservatives, perfumes, thickeners, opacifiers, conditioners, and buffering agents.

Cosmetic cleaning compositions in which the surface active agent consists essentially of the anionic ether sulfates of this invention have excellent foaming properties and low eye irritation. Therefore, no other surface active agent is required in the composition. Indeed, as shown in Tables 1 and 2, many of the compounds of this invention have eye irritation levels equivalent to a commercial baby shampoo and produce greater and more stable foams.

Although the anionic ether sulfates of the present invention provide satisfactory shampoos, other surface active agents, foam boosters or anti-irritants may be added without departing from this invention. These agents include amphoteric imidazolines, betaines, and cationic surface active agents which have been previously used to either increase foaming or decrease irritation levels.

In the following tables the foaming and eye irritation properties of a number of commercial shampoos, sodium alkyl sulfates and their corresponding sodium alkyl ether sulfates are compared. The eye irritation was measured by a modified Draize test. (Draize et al, Toilet Goods Assn. No. 17, May 1952, No. 1 Proc. Sci. Sect.) In the test, 0.1 ml. containing 20% of the test compound was added by dropper into one eye of an albino rabbit. The other eye served as a control. Three test rabbits were used for each solution. Measurements were made after 24, 48 and 72 hours.

Foam height was measured according to the Ross Miles test procedure (ASTM D1173-53). The tests were conducted in deionized water and hard water containing 300 ppm calcium. The foam height was measured at 50° C. with 0.1% of active ingredient. The foam height obtained initially and after 5 minutes is reported. The height of the foam after 5 minutes is a measure of foam stability.

TABLE 1

| EYE IRRITATION MEASURED BY MODIFIED DRAIZE TEST | | | |
|---|---|---|---|
| | 1 Day | 2 Days | 3 Days |
| | (Average Daily Score) | | |
| Commercial Products | | | |
| Baby Shampoo | 0.0 | 0.0 | 0.0 |
| Shampoo I | 53.0 | 60.0 | 63.7 |
| Shampoo II | 44.0 | 46.0 | 43.3 |
| Commercial lauryl (predominantly $C_{12}$) | | | |
| Sodium Lauryl Sulfate | 44.0 | 32.0 | 11.3 |
| Sodium Lauryl Ether (3) Sulfate | 40.7 | 24.0 | 5.3 |
| Sodium Lauryl Ether (12) Sulfate | 0.0 | 0.0 | 0.0 |
| Myristyl-cetyl ($C_{14}/C_{16}$) (60/40) | | | |
| Sodium $C_{14}/C_{16}$ (60/40) Alkyl Sulfate | 47.0 | 43.7 | 42.3 |
| Sodium $C_{14}/C_{16}$ (60/40) Alkyl Ether (6) Sulfate | 12.0 | 4.0 | 1.3 |
| Sodium $C_{14}/C_{16}$ (60/40) Alkyl Ether (12) Sulfate | 0.0 | 0.0 | 0.0 |
| Cetyl-stearyl ($C_{16}/C_{18}$) (65/35) | | | |
| Sodium $C_{16}/C_{18}$ (65/35) Alkyl Sulfate | 13.3 | 6.7 | 2.0 |
| Sodium $C_{16}/C_{18}$ (65/35) Alkyl Ether (3) Sulfate | 15.7 | 11.3 | 4.0 |
| Sodium $C_{16}/C_{18}$ (65/35) Alkyl Ether (6) Sulfate | 4.7 | 2.0 | 0.7 |
| Sodium $C_{16}/C_{18}$ (65/35) Alkyl Ether (12) Sulfate | 1.3 | 0.7 | 0.0 |
| Eicosyl ($C_{20+}$) | | | |
| Sodium $C_{20+}$ Alkyl Ether (12) Sulfate | 2.7 | 2.0 | 1.3 |
| Sodium $C_{20+}$ Alkyl Ether (12) Sulfate | 0.0 | 0.0 | 0.0 |

TABLE 2

| FOAM HEIGHTS (INITIAL AND AFTER 5 MIN.) | | | | |
|---|---|---|---|---|
| | Deionized Water | | 300 ppm Ca Hard Water | |
| | Initial | 5 Min. | Initial | 5 Min. |
| Commercial Products | | | | |
| Baby Shampoo | 165 | 144 | 107 | 83 |
| Shampoo I | 205 | 174 | 131 | 109 |
| Shampoo II | 190 | 160 | 161 | 135 |
| Commercial lauryl (predominantly $C_{12}$) | | | | |
| Sodium Lauryl Sulfate | 195 | 162 | 181 | 152 |
| Sodium Lauryl Ether (3) Sulfate | 191 | 167 | 200 | 177 |
| Sodium Lauryl Ether (12) Sulfate | 166 | 60 | 171 | 31 |
| Myristyl-cetyl ($C_{14}/C_{16}$) (60/40) | | | | |
| Sodium $C_{14}/C_{16}$ (60/40) Alkyl Sulfate | 207 | 182 | 149 | 137 |
| Sodium $C_{14}/C_{16}$ Alkyl Ether (3) Sulfate | 187 | 158 | 173 | 145 |
| Sodium $C_{14}/C_{16}$ Alkyl Ether (6) Sulfate | 170 | 160 | 170 | 160 |
| Sodium $C_{14}/C_{16}$ (60/40) Alkyl Ether (12) Sulfate | 149 | 96 | 158 | 123 |
| Cetyl-stearyl ($C_{16}/C_{18}$) (65/35) | | | | |
| Sodium $C_{16}/C_{18}$ (65/35) Alkyl Sulfate | 79 | 51 | 19 | 8 |
| Sodium $C_{16}/C_{18}$ (65/35) Alkyl Ether (3) Sulfate | 161 | 142 | 118 | 108 |
| Sodium $C_{16}/C_{18}$ (65/35) Alkyl Ether (6) Sulfate | 153 | 129 | 134 | 107 |
| Sodium $C_{16}/C_{18}$ (65/35) Alkyl Ether (12) Sulfate | 144 | 117 | 127 | 103 |
| Eicosyl ($C_{20+}$) | | | | |
| Sodium $C_{20+}$ Sulfate | 22 | 12 | Insoluble | |

The data reported in Tables 1 and 2 demonstrate that the eye irritation caused by alkyl sulfates decreases substantially as the number of ethoxy groups increases. It further reveals that the foam stability of commercial lauryl sulfate is not significantly affected by the addition of three ethoxy groups. Both sodium lauryl and sodium lauryl ether (3) sulfate have foaming properties which are equal to or better than the three commercial shampoos. However, the foam stability of sodium lauryl ether (12) sulfate is substantially lower than any of the commercial shampoos.

In sharp contrast, the foam stability of the $C_{14}$ to $C_{18}$ alkyl ether (12) sulfates is approximately equal to or better than the stability of the three commercial shampoos tested. In hard water, their foam stability is substantially better than the stability of the commercial baby shampoo, and their levels of eye irritation are equivalent to that of the baby shampoo.

We claim:

1. A high foaming, low eye irritation cosmetic cleaning composition comprising an alkyl ether sulphate consisting essentially of a mixture of 60% sodium myristyl ether (12) sulphate and 40% sodium cetyl ether (12) sulphate.

2. A high foaming, low eye irritation cosmetic cleaning composition comprising an alkyl ether sulphate consisting essentially of a mixture of 65% sodium cetyl ether (12) sulphate and 35% sodium stearyl ether (12) sulphate.

* * * * *